US008226622B2

(12) United States Patent
Mitchler et al.

(10) Patent No.: US 8,226,622 B2
(45) Date of Patent: Jul. 24, 2012

(54) INTERLABIAL ABSORBENT ARTICLE WITH SOLUBLE ADHESIVE AND TIME-DELAYED DISPERSION

(75) Inventors: Patricia Mitchler, Neenah, WI (US); Heather Sorebo, Appleton, WI (US); Susan Weyenberg, Appleton, WI (US); Ann Marie Przepasniak, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1526 days.

(21) Appl. No.: 10/326,912

(22) Filed: Dec. 20, 2002

(65) Prior Publication Data

US 2004/0122403 A1 Jun. 24, 2004

(51) Int. Cl.
*A61F 13/15* (2006.01)
*A61F 13/20* (2006.01)

(52) U.S. Cl. .................... 604/385.01; 604/367

(58) Field of Classification Search ............. 604/385.17, 604/364, 358, 365, 385.01; 128/113.1; 523/111; 428/354
See application file for complete search history.

(56) References Cited

U.S. PATENT DOCUMENTS

| | | | |
|---|---|---|---|
| 3,726,277 A | 4/1973 | Hirschman | |
| 3,756,232 A * | 9/1973 | Noguchi et al. ............. | 604/359 |
| 3,891,584 A | 6/1975 | Ray-Chaudhuri et al. | |
| 3,983,873 A | 10/1976 | Hirschman | |
| 4,175,561 A | 11/1979 | Hirschman | |
| 4,522,967 A * | 6/1985 | Sheldon et al. ............. | 524/377 |
| 4,600,404 A | 7/1986 | Sheldon et al. | |
| 5,429,631 A | 7/1995 | Grenier | |
| 5,484,429 A | 1/1996 | Vukos et al. | |
| 5,509,913 A * | 4/1996 | Yeo .............................. | 604/364 |
| 5,573,523 A | 11/1996 | Whalen et al. | |
| 5,605,764 A * | 2/1997 | Miller et al. ................. | 428/480 |
| 5,613,964 A * | 3/1997 | Grenier .................... | 604/385.01 |
| 5,681,299 A | 10/1997 | Brown | |
| 5,762,644 A | 6/1998 | Osborn, III et al. | |
| 5,891,126 A | 4/1999 | Osborn, III et al. | |
| 5,948,710 A | 9/1999 | Pomplun et al. | |
| 5,952,251 A | 9/1999 | Jackson et al. | |
| 6,033,391 A | 3/2000 | Osborn, III et al. | |
| 6,171,292 B1 | 1/2001 | Osborn, III et al. | |
| 6,183,456 B1 | 2/2001 | Brown et al. | |

(Continued)

FOREIGN PATENT DOCUMENTS

EP 0781538 7/1997

(Continued)

OTHER PUBLICATIONS

EPO Search Report, Dec. 2, 2003.

(Continued)

*Primary Examiner* — Michele M Kidwell
(74) *Attorney, Agent, or Firm* — Dority & Manning, P.A.

(57) ABSTRACT

An interlabial absorbent article configured for disposition primarily within the vestibule of a female wearer includes a generally liquid permeable cover sheet, a generally liquid impermeable back sheet, and an absorbent material disposed between the cover sheet and the back sheet. A time-delayed water soluble adhesive combination joins the cover sheet and back sheet together with the absorbent material sandwiched therebetween. The adhesive combination is configured so as to maintain structural integrity of the article for a time period of at least about two hours after the article is immersed in water by being flushed while ensuring that the article breaks up within about 24-72 hours after flushing.

15 Claims, 3 Drawing Sheets

U.S. PATENT DOCUMENTS

| | | |
|---|---|---|
| 6,232,521 B1 | 5/2001 | Bewick-Sonntag et al. |
| 6,270,486 B1 | 8/2001 | Brown et al. |
| 6,444,761 B1 * | 9/2002 | Wang et al. .................. 525/404 |
| 6,514,602 B1 | 2/2003 | Zhao et al. |
| 7,138,560 B2 | 11/2006 | Przepasniak et al. |
| 2001/0000796 A1 | 5/2001 | Osborn, III et al. |
| 2001/0001815 A1 | 5/2001 | Osborn, III et al. |
| 2001/0008964 A1 * | 7/2001 | Kurata et al. ................. 604/364 |
| 2001/0025163 A1 | 9/2001 | Brown et al. |
| 2002/0058921 A1 | 5/2002 | Sigl |
| 2003/0225388 A1 | 12/2003 | Bhavani |
| 2004/0018366 A1 | 1/2004 | George et al. |
| 2004/0019168 A1 | 1/2004 | Soerens et al. |
| 2004/0043688 A1 | 3/2004 | Soerens et al. |
| 2004/0122403 A1 | 6/2004 | Mitchler et al. |

FOREIGN PATENT DOCUMENTS

| | | |
|---|---|---|
| EP | 0835337 | 10/2001 |
| EP | 0989837 | 4/2002 |
| EP | 0989837 B1 * | 10/2002 |
| WO | 9518191 | 7/1995 |
| WO | 9808475 | 3/1998 |
| WO | WO 9808475 A1 * | 3/1998 |
| WO | 9926574 | 6/1999 |
| WO | 9956689 | 11/1999 |
| WO | 0166160 | 9/2001 |
| WO | 2004011046 A1 | 2/2004 |
| WO | 2004060248 A1 | 7/2004 |

OTHER PUBLICATIONS

U.S. Appl. No. 10/732,163, filed Dec. 10, 2003.
U.S. Appl. No. 10/732,827, filed Dec. 10, 2003.
EPO Search Report, Mar. 31, 2004.

* cited by examiner

INTERLABIAL ABSORBENT ARTICLE WITH SOLUBLE ADHESIVE AND TIME-DELAYED DISPERSION

FIELD OF THE INVENTION

The present invention relates to the field of feminine hygiene products, and more particularly to interlabial absorbent articles.

BACKGROUND

A broad range and wide variety of absorbent articles configured for absorption of bodily exudates such as menstrual fluid are well known. With respect to feminine hygiene, the art has offered two basic types of feminine hygiene protection: namely sanitary napkins and panty liners, developed for external wear about the pudendum region, and tampons, developed for placement within the vaginal cavity, and accordingly for interruption of menstrual flow therefrom prior to such menstrual flow reaching the vestibule. Hybrid feminine hygiene protection devices, attempting to merge the structural features of both sanitary napkins and tampons in a single type of device, have also been proposed, but have not seen a meaningful measure of acceptance.

Other less intrusive devices, known as labial or interlabial devices or pads, have also been proposed. These articles are designed to reside primarily within the wearer's vestibule while having a portion residing at least partially external of the wearer's vestibule. Interlabial articles can provide a preferred profile of appearance when viewed through a wearer's outer garments and do not have the same problem of reliance on swelling within the vaginal canal as required by tampons. U.S. Pat. Nos. 5,484,429; 4,175,561; 3,983,873; and 3,726,277 disclose various types of interlabial absorbent articles.

Interlabial absorbent articles are generally designed to be expelled by the urine stream when the wearer urinates. The article thus falls into a conventional toilet where it can be flushed. The relatively small size of interlabial devices facilitates flushing in conventional sewer and septic systems. However, care must still be taken that the articles disperse in the sewer or septic system so as not to obstruct or otherwise damage the system. In this regard, efforts have been made in the art to provide interlabial articles that dissipate or disperse quickly in water. For example, U.S. Pat. No. 6,171,292 B1 describes an interlabial absorbent article that is designed so that the components of the article fragment within at least two hours of exposure to mildly agitated room temperature water. Alternately, the components may separate from each other without themselves fragmenting. The '292 patent teaches that it would be most preferred if the article fragmented within about 15 minutes. U.S. Pat. No. 5,573,523 describes a biodegradable and flushable mini-pad formed entirely of cellulosic materials. The outer panels are mechanically bonded at their perimeters without an adhesive to enhance biodegradation of the pad.

However, the desire for an interlabial absorbent article that disperses quickly in water may conflict with performance requirements for the article. Due to the relatively high water content of viscous and vaginal fluids, use of a water soluble adhesive (or no adhesive at all) that immediately starts to dissolve and cause the article to break up could sacrifice the seal strength and product integrity while in use. Wearing time of the product may also be reduced if the article tends to break apart prior to being expelled upon urination as intended. Absorbent articles that tend to fragment into individual components before or during flushing may also tend to cause clogging of a structure's plumbing system. The more components or articles that "travel" through a home's contorted plumbing system per absorbent article flushed increases the risk that any one such component may become entrapped or entangled on roots or the like, as compared to a single intact article.

Thus, a need exists for an interlabial absorbent article design that offers the benefits of a dispersible product without sacrificing performance of the article or adding to the risk of plumbing clogs or other problems upon flushing the article.

SUMMARY

Objects and advantages of the invention will be set forth in part in the following description, or may be obvious from the description, or may be learned through practice of the invention.

The present invention relates to a unique configuration for a feminine care interlabial absorbent article that offers distinct advantages over conventional devices. The interlabial absorbent article includes a generally liquid permeable cover sheet, a generally liquid impervious back sheet, and an absorbent material disposed between the cover sheet and back sheet. A time-delayed water soluble adhesive combination is used at least in part as the construction adhesive for the article and is disposed to join the cover sheet and the back sheet together with the absorbent material sandwiched therebetween. The adhesive combination is formulated so as to maintain structural integrity of the article for a time period of at least about two hours after the article is immersed in water by being flushed while ensuring that the article fragments or breaks-up into at least two constituent components within about 24-72 hours after immersion.

It should be appreciated that a water insoluble adhesive may also be used in construction of the article. For example, a water soluble adhesive may be placed between the cover sheet and absorbent material, and a water insoluble adhesive may be placed between the back sheet and absorbent material. Likewise, a water insoluble adhesive may be placed between the cover sheet and absorbent material, and a water soluble adhesive may be placed between the back sheet and absorbent material.

In one embodiment, the article fragments upon the adhesive combination dissolving such that the cover sheet separates completely from the back sheet. In another embodiment the cover sheet and back sheet do not necessarily need to completely separate. For example, the adhesive combination may be disposed around a circumference of the article between the cover sheet and back sheet such that the cover sheet separates from said back sheet around at least a portion of the circumference upon the adhesive combination dissolving. The absorbent material may be dispersible in water and disperses out of the article upon the cover sheet and the back sheet separating around a portion of the circumference.

The adhesive combination may be applied by any conventional technique and at any suitable location within the article. For example, the adhesive combination may be applied as a meltblown spray generally uniformly between the absorbent material and an inner face of the back sheet, and/or between the absorbent material and an inner face of the cover sheet. The adhesive may be applied as a continuous uniform coating or in any desired pattern. In particular embodiments, the water soluble adhesive combination is the only adhesive used in the article. In alternate embodiments, an additional water insoluble adhesive may be used. For example, the absorbent material may be dispersible in water and be attached to the back sheet and/or cover sheet with a water insoluble adhesive.

The cover sheet may be attached to the back sheet around a circumference of the article with the water soluble adhesive combination according to the invention such that when the adhesive combination dissolves, the cover sheet separates from the back sheet around at least a portion of the circumference and the absorbent material is free to disperse out of the article. If the cover sheet is not otherwise attached to the absorbent material, it will completely separate from the article.

In still an alternate embodiment, the adhesive combination may be disposed as discrete areas of a water soluble adhesive interspaced between discrete areas of a water insoluble adhesive. Once the water soluble adhesive dissolves, the dispersible absorbent material is free to disperse from the article along the spaces or channels between the water insoluble adhesive. The spaces are sized so as to control the rate at which the absorbent material disperses. At least a portion of the circumferential seal between the cover sheet and back sheet would also dissolve so that the absorbent material may disperse out of the article.

The adhesive combination according to the invention may be formulated in various ways to achieve the desired "time-delay" characteristic. For example, the adhesive combination may include a time release agent or additive, the additive preventing the adhesive from substantially dissolving before the time period of at least about two hours. In another embodiment, the adhesive combination may include a water soluble adhesive applied in an amount sufficient to ensure that the article is held intact for the time period of at least about two hours. For example, the adhesive may be applied in a sufficient thickness or pattern such that not all of the adhesive is exposed to water upon immersion of the article, but at least a portion of the adhesive is only exposed after another overlying portion of the adhesive dissolves.

The adhesive combination may include a mixture of a water soluble adhesive and a water insoluble adhesive combined in a ratio such that the water solubility strength of the adhesive combination is sufficient to ensure that the article is held intact for the time period of at least about two hours.

The present invention also includes various embodiments of a method for forming an interlabial absorbent article that is dispersible in water after at least about two hours.

Aspects of the invention will be described in greater detail below by reference to embodiments illustrated in the attached drawings.

DETAILED DESCRIPTION

Figure 1:
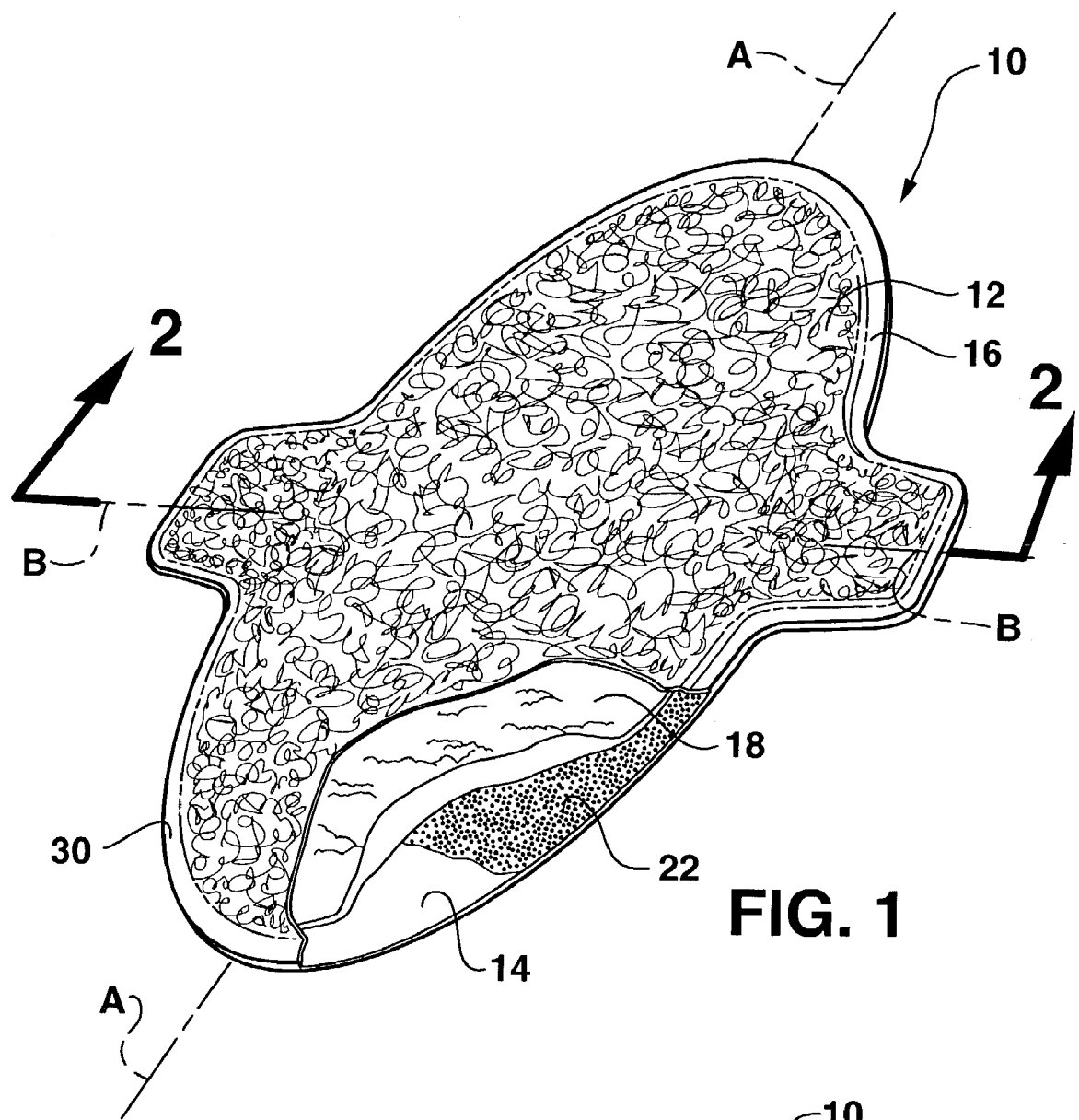
FIG. 1 is a perspective and partial cut-away view of an interlabial absorbent article in accordance with the invention.

Reference will now be made in detail to embodiments of the invention, one or more examples of which are illustrated in the drawings. Each embodiment and example are provided for purposes of explaining the invention, and are not meant as a limitation of the invention. For example, features illustrated or described as part of one embodiment may be used with another embodiment to yield still a further embodiment. It is intended that the present invention include these and other modifications and variations as come within the scope and spirit of the invention.

As used herein the term "dispersible" means that the fibers of a material are capable of debonding, resulting in the material breaking down into smaller pieces than the original sheet. Debonding is generally a physical change of scattering or separation, as compared to a state change, such as dissolving, wherein the material goes into solution, e.g., a water soluble polymer dissolving in water.

As used herein, the term "flushable" means that an article, when flushed down a conventional commode containing approximately room temperature water, will pass through the commode plumbing, the sewer lateral (i.e., the piping between the house or building and the main sewer line) without clogging.

As used herein, the term "water dispersible" refers to a fibrous nonwoven composite structure which when placed in an aqueous environment will, with sufficient time, break apart into smaller pieces. As a result, the structure once dispersed may be more advantageously processable in recycling processes or flushable in, for example, septic and municipal sewage treatment systems. If desired, such fibrous nonwoven structures may be made more water-dispersible or dispersion may be hastened by the use of agitation and/or certain triggering means.

As used herein, the term "water soluble" refers to a state change of a material or composition when exposed to an aqueous environment, such as dissolving, wherein the material goes into solution, e.g., a water soluble polymer or water soluble adhesive dissolving in water.

As used herein, the term "interlabial absorbent article" refers to a device having at least one absorbent component, and which is specifically configured for disposition between the labia majora, extending at least partially into the vestibule of a female wearer during use. The vestibule is considered to be the region defined within the labia beginning at about a point lying caudally from the anterior labial commissure and extending rearward to the posterior labial commissure, and bounded inwardly by the floor of the vestibule. One of skill in the art fully understands that there is a wide range of variation among women with respect to the relative size and shape of labia majora and labia minora as the same interrelatedly define the contour of the vestibule. For purposes of the present description, however, such differences will not specifically be addressed, it being recognized that in any event the disposition of the absorbent article into the vestibule necessitates placement between the labia majora regardless of any such consideration respecting the labia minora. An interlabial absorbent article is disposed at least partially within the vestibule for partially occluding the vestibule with respect to fluid flow from the vestibule. In this regard, the predominant use of the absorbent article is for the absorption of menstrual or intermenstrual fluid emitted via the vaginal orifice, although the article is equally well adapted to serve as a type of incontinence device for absorption of urine as occurs upon minor, female incontinence.

The present invention provides an interlabial absorbent article configured for disposition primarily within the vestibule of a female wearer. The article may take on any suitable overall shape and configuration, and is illustrated in the figures as a simple oval shape for explanation purposes only. The article includes a liquid permeable cover sheet, a generally liquid impermeable back sheet, and an absorbent material disposed between the cover sheet and back sheet. A construction adhesive combination is used to retain the components together as a coherent unit with the cover sheet and back sheet sealed around a circumference of the article. The cover sheet and back sheet may be joined to at least a portion of the absorbent material. The adhesive combination is specifically formulated to ensure that the article does not disperse or fragment into individual components for at least about two hours after the article is exposed to an aqueous environment, for example after being dropped into a toilet and flushed. Embodiments of the adhesive combination are described in greater detail below.

After about two hours or more of mildly agitated exposure to room temperature water, the article looses structural integrity such that it disperses or breaks-up into at least two components. For example, the cover sheet may be completely removed from the back sheet and absorbent material. The article is also considered to have lost structural integrity if the seal between the cover sheet and back sheet opens or separates enough so that the absorbent material may disperse out from between the sheets. Thus, the sheets may still be at least partially attached. It is also within the scope and spirit of the invention that the individual components are also dispersible. For example, the absorbent material may be a water dispersible absorbent composite structure. The individual components may also be biodegradable.

Various advantages may be achieved with an interlabial absorbent article according to the invention. For example, the product may be used for an extended period under conditions where it is exposed to bodily fluids having a high water content without worry that the product will prematurely fail either by coming apart or causing premature leakage because of poor product integrity. The article will eventually disperse in or before it reaches a municipal water sewage treatment plant. The article will be conveyed after flushing through a structure's plumbing system as a single component, thus minimizing the chance of clogging that exists with multiple components flowing through the system. If the product does become clogged as a single unit, it will eventually disperse and may become unclogged.

Referring to the figures in general, various embodiments of an interlabial absorbent article 10 are illustrated. The absorbent article 10 includes a cover sheet 12, a back sheet 14, and an absorbent material 18 sandwiched between the cover sheet 12 and back sheet 14. The cover sheet 12 and back sheet 14 are sealed together at their edges 16, the sealed edges 16 defining an overall circumference 20 and geometry for the article 10. The article 10 should be of a suitable size and shape which allows at least a portion, preferably a major portion, of the absorbent article to be disposed within the vestibule of a female wearer. In addition, the absorbent article 10 desirably at least partially occludes and intercepts the flow of menstrual fluid, urine or other bodily exudates from the wearer's vaginal orifice and/or urethral orifice.

The article 10 is not limited to any particular shape or configuration. In the illustrated embodiments, for example, the article 10 has an overall "butterfly" shape (oval with lateral tab portions). One skilled in the art will readily appreciate, however, that other geometries may also be suitable, including, for example, rectangular, ovoid-like, elliptical, trapezoidal, circular-like, triangular, square-shaped, teardrop-shaped, diamond-shaped, butterfly, pear-shaped, heart-shaped or a variety of combinations thereof. In addition, tabs or wings may be used with any of the overall geometries. Non-limiting examples of shapes for the tab include, ovoid, elliptical, trapezpoidal, rectangular, triangular, diamond-shaped, circular, semi-circular, or any combination of the above.

All or a portion of the components of the article 10 may be made of biodegradable materials.

The geometry of the absorbent material 18 is a significant factor affecting the overall size, shape, and effectiveness of the absorbent article 10. In general, the absorbent material 18 has a maximum width and a minimum width as measured in the transverse plane of axis B. For a circular or rectangular shaped article 10, the maximum and minimum widths are the same. In the embodiment of FIG. 1, the maximum width is defined at the transverse axis B and decreases towards the longitudinal ends of the article. The maximum width of the absorbent 18 typically is no greater than about 30 mm; alternatively, no greater than about 40 mm; alternatively, no greater than about 50 mm; alternatively, no greater than about 60 mm; or alternatively, no greater than about 70 mm. The minimum width of the absorbent 18 typically is no less than about 30 mm; alternatively, no less than about 20 mm; alternatively, no less than about 10 mm; or alternatively, no less than about 5 mm. Thus, the absorbent material 18 can have a width ranging from no less than about 5 mm up to no greater than about 70 mm; although the approximate width(s) of the absorbent can vary according to, inter alia, the general design and intended disposition of the absorbent article 10 within the vestibule of a female wearer.

The absorbent material 18 also has a maximum length measured along the principal longitudinal axis A of the article. The maximum length of the absorbent material 18 typically is no greater than about 40 mm; alternatively, no greater than about 50 mm; alternatively, no greater than about 60 mm; alternatively, no greater than about 70 mm; alternatively, no greater than about 80 mm; alternatively, no greater than about 90 mm; or alternatively, no greater than about 120 mm.

The absorbent article 10 is desirably provided with sufficient capacity to absorb and retain the intended amount and type of bodily exudate(s). The absorbent capacity is provided by a fluid retentive core made up of the absorbent material 18. The absorbent material 18 can have an absorbent capacity ranging from no less than about 1 g/g up to no greater than about 30 g/g; although the approximate capacity of the absorbent can vary according to, inter alia, the general design and intended disposition of the absorbent article 10 within the vestibule of a female wearer. One of skill in the art will readily realize that the addition of superabsorbent polymer or coated superabsorbent polymer) to the absorbent material 18 typically has the effect of substantially increasing the absorbent capacity.

Further, the size and absorbent capacity of the absorbent material 18 can be varied with the dimension, shape, and configuration of the absorbent material. For example, the absorbent can have a varying thickness with in the article 10, or can have a hydrophilic gradient, or can contain superabsorbent polymer(s) and the like. The flat absorbent material 18 will generally have a thickness of about 10 mm or less with a preferred flat thickness of about 3 mm and folded thickness of about 6 mm or less; although the approximate thickness of the absorbent can vary according to, inter alia, the general design and intended disposition of the absorbent article 10 within the vestibule of a female wearer.

The absorbent material 18 can include any material capable of absorbing and/or adsorbing and thereafter retaining the intended bodily exudate(s). Suitable materials are also generally hydrophilic, compressible and conformable. The absorbent material 18 can be formed from any of the materials well known to those of ordinary skill in the art. Examples of such materials include, but are not limited to, various natural or synthetic fibers, multiple plies of creped cellulose wadding, fluffed cellulose fibers, rayon or other regenerated cellulose materials, wood pulp fibers or comminuted wood pulp fibers, airlaid material, textile fibers, a blend of polyester fibers and polypropylene fibers, absorbent foams, absorbent sponges, superabsorbent polymers, coated superabsorbent polymers, fibrous bundles or nits, or any equivalent material or combination of materials. Hydrophobic materials are also suitable for use where the hydrophobic material has been rendered hydrophilic according to any of a number of known methods for so doing.

The absorbent material 18 desirably also has a relatively low density which is desirable for comfort. Generally, the absorbent material 18 has a density that can range up to about 0.5 g/cc; although the approximate density of the absorbent can vary according to, inter alia, the general design and intended disposition of the absorbent article 10 within the vestibule of a female wearer.

The absorbent material 18 can have a basis weight of about 600 gsm or less; with a preferred basis weight of about 250 to about 400 gsm; although the approximate basis weight of the absorbent can vary according to, inter alia, the general design and intended disposition of the absorbent article 10 within the vestibule of a female wearer.

A specific example of a suitable absorbent is a coform material made of a blend of polypropylene and cellulose fibers such as that used in KOTEX® pantiliners and obtainable from Kimberly-Clark Corporation, Neenah, Wis., USA.

In a particular embodiment of the article 10 in accordance with the invention, the absorbent material 18 is dispersible in water. Cellulosic fiber webs are generally considered dispersible in water in that they readily fragment into individual fibers upon sufficient exposure to an aqueous environment. Various other water dispersible absorbent materials are known to those skilled in the art and may be used with the present invention. For example, U.S. Pat. Nos. 5,952,251 and 5,948,710, such patents incorporated herein by reference for all purposes, describe absorbent dispersible coform materials that may be suitable for the present invention. U.S. Pat. No. 6,171,292 B1, incorporated herein by reference for all purposes, also discloses a number of dispersible absorbent materials that may be used with the present invention.

Figure 3:
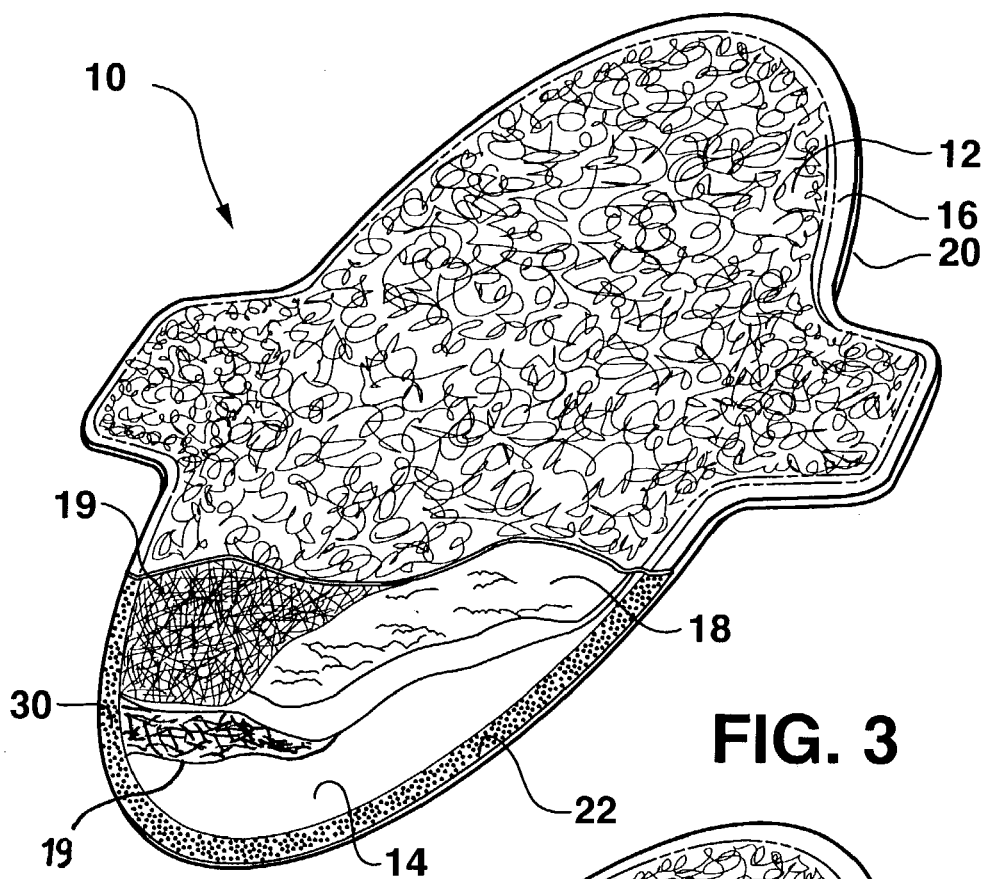
FIG. 3 is a perspective and partial cut-away view of an alternate embodiment of an interlabial absorbent article in accordance with the invention.

In particular embodiments, the absorbent material may be wrapped in a layer of material 19 which may be, for example, a tissue layer or soluble polymer layer, as seen in FIG. 3. Alternately, the layer 19 may be disposed only between the absorbent material 18 and cover sheet 12, or only between the absorbent material 18 and back sheet 14. In a particular embodiment, the material 19 is disposed between the absorbent material 18 and back sheet 14 with the water soluble adhesive or a water insoluble adhesive between the layer 19 and back sheet 14.

The fluid permeable cover sheet 12 has an outwardly facing surface that may contact the body of the wearer and receive bodily exudate(s). The cover sheet 12 desirably is made of a material which is flexible and non-irritating to the tissues within the vestibule of a female wearer. As used herein, the term "flexible" is intended to refer to materials which are compliant and readily conform to the bodily surface(s) with which such materials are in contact, or materials which respond by easily deforming in the presence of external forces.

The cover sheet 12 is provided for comfort and conformability and functions to direct bodily exudate(s) away from the body, through the cover sheet 12 and toward the absorbent material 18. The cover sheet 12 should retain little or no liquid in its structure so that the cover provides a relatively comfortable and non-irritating surface next to the tissues within the vestibule of a female wearer. The cover sheet 12 can be constructed of any woven or nonwoven material which is easily penetrated by bodily fluids which contact the surface of the cover. Examples of suitable cover materials include rayon, bonded carded webs of polyester, polypropylene, polyethylene, nylon, or other heat-bondable fibers, polyolefins, such as copolymers of polypropylene and polyethylene, linear low-density polyethylene, and aliphatic esters such as polylactic acid. Finely perforated film webs and net material can also be used. A specific example of a suitable cover material is a bonded carded web made of polypropylene and polyethylene such as that used as cover stock for KOTEX® pantiliners and obtainable from Sandler Corporation, Germany. Other examples of suitable materials are composite materials of polymer and nonwoven fabric materials. The composite materials are typically in the form of integral sheets generally formed by the extrusion of a polymer onto a web of spunbonded material. The fluid permeable cover 12 can also contain a plurality of apertures (not shown) formed therein which are intended to increase the rate at which bodily fluid(s) can penetrate through the cover and into the absorbent material 18.

A physiologically hydrous cover sheet material is also suitable for use. As used herein, the phrase "physiologically hydrous" is intended to connote a sheet material which maintains a suitably moist interface between the tissues of the vestibule and the absorbent article 10 when disposed in the vestibular environment; material which is benign respecting the requirements of comfort associated with the interposition of fabric or fabric-like structures within the moist tissue environment of the vestibule, also considering that the absorbent article receives bodily fluid(s) migrating through the vestibule and conducts such fluids to the absorbent material 18. Thus, while the cover sheet 12 is not "hydrous" in the classic sense prior to use, inasmuch as the sheet is dry at that time, the cover sheet 12 maintains, or at least does not interfere with the maintenance of, the proper moisture level or moisture balance required within the vestibule for proper maintenance of tissue health within the vestibule.

At least a portion of the surface of the cover sheet 12 can be treated with a surfactant in order to render the cover more hydrophilic. This results in permitting the insulting bodily fluid(s) to more readily penetrate the material The surfactant can also diminish the likelihood that the insulting bodily fluid(s), such as menstrual fluid, will flow off the cover sheet 12 rather than passing through the cover and being absorbed by the absorbent material 18. One suitable approach provides for the surfactant to be substantially evenly distributed across at least a portion of the upper surface of the cover sheet 12 which overlies the upper surface of the absorbent material 18.

The cover sheet 12 may also be embossed with any desired embossing pattern. Embossing techniques are well known to those skilled in the art. An embossing pattern not only creates an aesthetically pleasing surface, but the resulting embossed channels facilitate intake of menses fluid. Menses will tend to flow along the densified edges of the channels rather than pool on contact points of the cover sheet 12.

The cover sheet 12 can be maintained in secured relation with the absorbent material 18 by adhering all or a portion of the adjacent surfaces to one another with any pattern of the adhesive combination according to the invention. The materials may be joined by entangling at least portions of the adjacent surface of the absorbent material 18 with portions of the adjacent surface of the cover sheet 12. For embodiments wherein the absorbent material is dispersible, portions of the cover sheet 12 may be fused or bonded to the adjacent surface of the absorbent material 18, or adhered with a water insoluble adhesive.

The back sheet 14 typically resides on the lower surface of the absorbent material 18 as the absorbent article 10 is worn by a wearer, and can be constructed from any desired material which may be generally liquid-impermeable (although not required). Desirably, the back sheet 14 permits passage of air and moisture vapor out of the absorbent 10 while blocking passage of bodily fluid(s). An example of a suitable material is a micro-embossed, polymeric film, such as polyethylene, polypropylene or polyester, having a minimum thickness of no less than about 0.025 mm and a maximum thickness of no greater than about 0.13 mm. Bicomponent films can also be used, as well as woven and nonwoven fabrics which have been treated to render such fabrics liquid-impermeable. An example of another suitable material is a closed cell polyolefin foam, for example, a closed cell polyethylene foam. A specific example of a back sheet material is a polyethylene film such as that used in KOTEX® pantiliners and obtainable from Pliant Corporation, Schaumburg, Ill., USA.

The back sheet 14 can be maintained in secured relation with the absorbent material 18 by application of the adhesive combination 22 according to the invention. For example, the adhesive combination 22 may be applied in any desired pattern between the backsheet 14 and absorbent material 18. With embodiments wherein the absorbent material is dispersible, the materials may be secured by bonding all or a portion of the adjacent surfaces to one another. A variety of bonding methods known to one of skill in the art can be utilized to achieve any such secured relation. Examples of such methods include, but are not limited to, ultrasonic bonding, thermal bonding, or the application of adhesive materials in a variety of patterns between the two adjoining surfaces.

Figure 2:
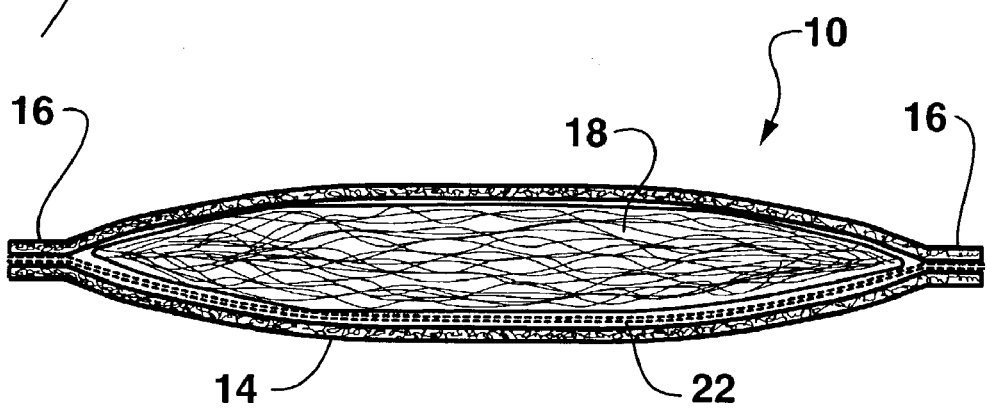
FIG. 2 is a cross-sectional view of the article of FIG. 1 taken along the lines indicated.

The cover sheet 12 and back sheet 14 have periphery edges joined together to form a sealed circumferential edge 16 around the circumference 20 of the article 10. The absorbent combination 22 is used to seal the edges of the cover sheet 12 and back sheet 14. In one embodiment as illustrated in FIGS. 1 and 2, the adhesive combination 22 is applied generally uniformly over the inner surface of the back sheet 14 so as to extend generally completely to the edge of the sheet 14. The absorbent material structure 18 is slightly smaller than the dimensions of the back sheet 14 and cover sheet 12 and thus a circumferential border 30 of the adhesive combination 22 is defined. The cover sheet 12 is adhered to the back sheet 14 at this border to define a sealed edge 16 of the article 10. Although not illustrated in the figure, it should be appreciated that the adhesive combination 22 may also be used to join the cover sheet 12 to the absorbent material 18, as described above.

In the embodiment of FIG. 3, the adhesive combination 22 is applied generally only as a circumferential band 30 and is intended primarily to join the cover sheet 12 and back sheet 14 around the sealed edges 16 of the article. With this embodiment, the cover sheet 12 and back sheet 14 will completely detach from each other after a sufficient immersion time of the article in water has caused the adhesive combination 22 to dissolve. If the cover sheet 12 and back sheet 14 are not otherwise attached to the absorbent material 18, the components will detach from each other. In the case of a dispersible absorbent material 18, the cover sheet 12 and back sheet 14 may be secured to the absorbent material 18 by any other suitable adhesive or technique. Once the adhesive combination 22 dissolves, the dispersible absorbent material will disperse out from around the edge 16 of the article 10. The cover sheet 12 and back sheet 14 will separate after the absorbent material has sufficiently dispersed.

Figure 4:
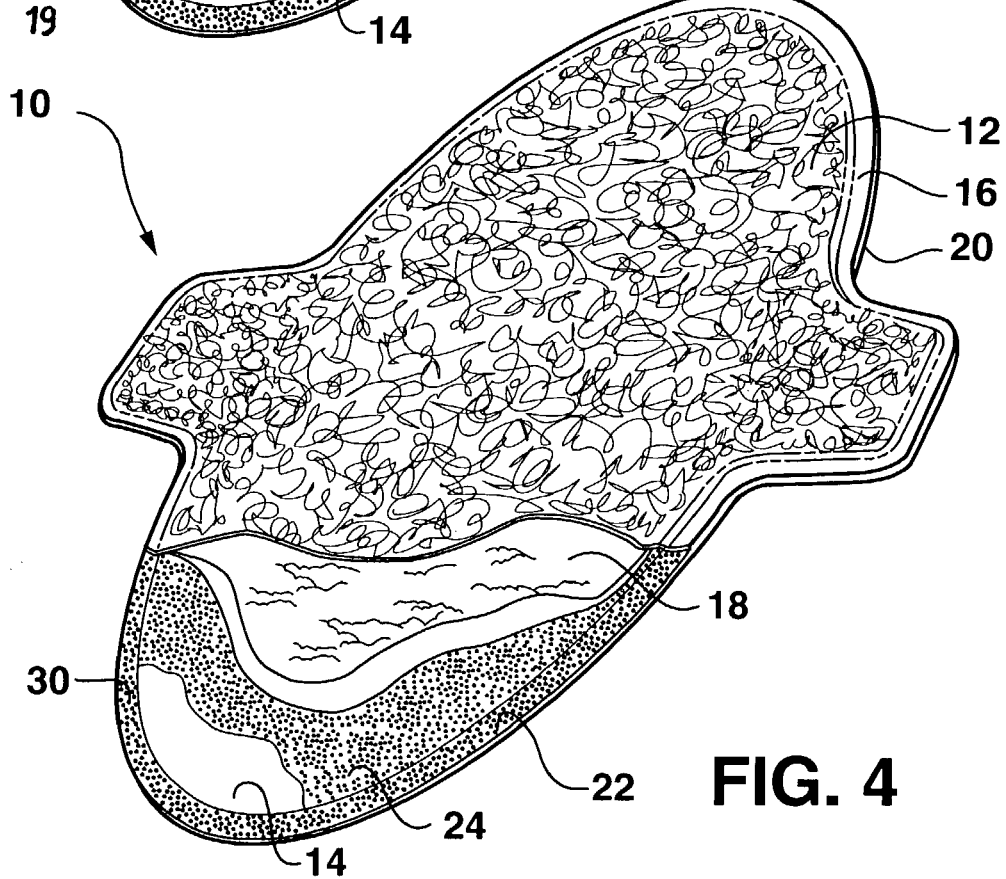
FIG. 4 is a perspective and partial cut-away view of an alternate embodiment of an interlabial absorbent article in accordance with the invention.

The embodiment of FIG. 4 is similar to that of FIG. 3 and includes a water insoluble adhesive 24 applied between the absorbent material 18 and back sheet 14 inside of the border 30 of adhesive combination 22. Although not illustrated in the figure, the water insoluble adhesive 24 may also be used to join the cover sheet 12 to the absorbent material 18. As described above with respect to FIG. 3, once the border 30 of adhesive combination 22 dissolves, the edge seal 16 is broken and the dispersible absorbent material 18 will disperse out of the article 10. The cover sheet 12 may detach immediately after the adhesive combination 22 dissolves if it is not otherwise attached to the absorbent material 18.

Figure 5:
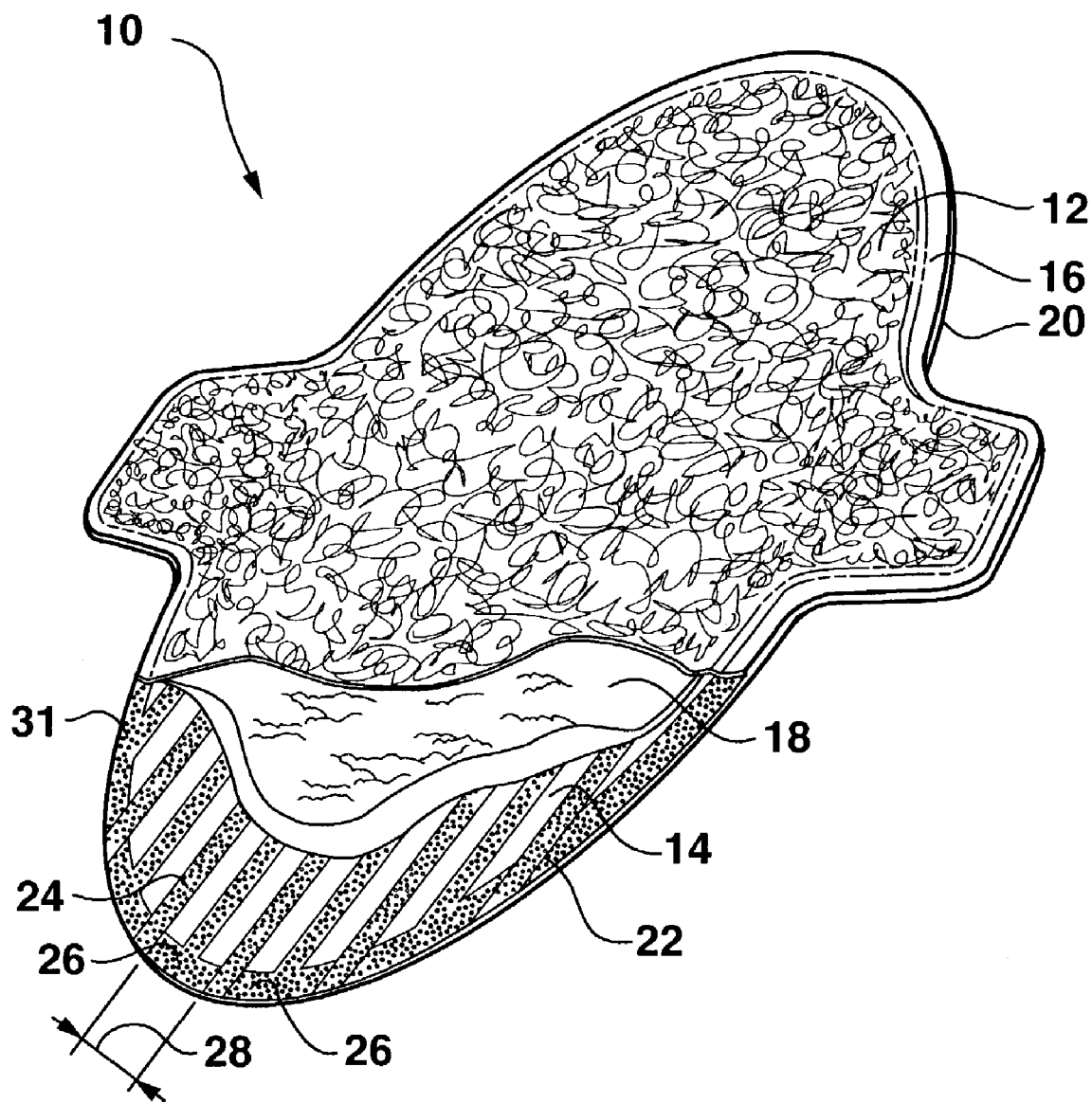
FIG. 5 is a perspective and partial cut-away view of an alternate embodiment of an interlabial absorbent article in accordance with the invention.

In an alternate embodiment, the adhesive combination may be defined by discrete areas of a water soluble adhesive spaced from discrete areas of a water insoluble adhesive. Referring to FIG. 5, such an embodiment may be defined by bands or stripes of a water insoluble adhesive 24 interspaced between bands or stripes of a water soluble adhesive 26 such that a space 28 is defined between the bands of water insoluble adhesive 24. The water soluble adhesive 26 may also be provided as circumferential band segments 31 between the bands of insoluble adhesive 24 to seal the edges 16 of the cover sheet 12 and back sheet 14 between the bands 24. With this embodiment, the spacing 28 may be designed such that the water soluble adhesive 26 need not be "time-delayed." Upon immersion of the article 10, the water soluble adhesive 26 will dissolve relatively quickly such that the sealed edge 16 is undone between the bands of insoluble adhesive 24. The spacing 28 is, however, designed to be relatively narrow and the dispersible absorbent material 18 cannot readily disperse from between the sheets 12, 14. The spacing 28 may be empirically determined to ensure that the absorbent material does not substantially disperse until after about two hours. It should be appreciated that any number of patterns of discrete areas of water soluble adhesive and water insoluble adhesive may be devised to accomplish the desired time delay, the stripe pattern of FIG. 5 being exemplary only.

The water soluble adhesive combination used in articles according to the invention may be formulated in various ways. For example, the adhesive combination may include a time release agent or additive that essentially renders the adhesive combination water insoluble for the desired delay time, after which the adhesive dissolves in water. This agent or additive may be mixed homogeneously with the adhesive and, in essence, results in a "slow" soluble adhesive. In other words, the adhesive may be water soluble, but at such a rate that the article is held together for the desired delay period. A suitable time delay adhesive is available from National Starch Corp. of New Jersey, USA, having a product identification code of 34-731A.

In another embodiment, the adhesive combination may include a water soluble adhesive applied in an amount sufficient to ensure that the article is held intact for the time period of at least about two hours. For example, the adhesive may be applied in a sufficient thickness or pattern such that not all of the adhesive is exposed to water upon immersion of the article, but at least a portion of the adhesive is only exposed after another overlying portion of the adhesive dissolves. Applicant has found that an acceptable water soluble adhesive that may be applied in sufficient amounts to achieve the desired time delay is National Starch 427A available from National Starch and Chemical Corp., New Jersey, USA. The amount (i.e., in gsm) of adhesive required may be readily empirically determined, and will depend in large part on the shape and size of the interlabial article, deposition pattern of the adhesive, etc. For the National Starch 427A adhesive, the add on level may be between about 8 gsm to about 20 gsm.

The adhesive combination may include a mixture of a water soluble adhesive and a water insoluble adhesive combined in a ratio such that the water solubility strength of the adhesive combination is sufficient to ensure that said article is held intact for said time period of at least about two hours. Ratios may be empirically determined by those skilled in the art, and will be dependent on the characteristics of the water soluble adhesive and the water insoluble adhesive. Suitable water soluble adhesives are describe, for example, in U.S. Pat. Nos. 6,444,761; 4,600,404; 4,522,967; and 3,891,584, such references incorporated herein by reference for all purposes. The publication WO 95/181191 also describes water-dispersible adhesive compositions that may be useful in the present invention.

The following Test Protocol describes a method that may be used to determine how quickly an interlabial absorbent article disperses after being dropped into a toilet and flushed.

Test Procedure

This protocol measures the ability of Interlabial pads to clear a toilet fixture and in-house plumbing and allows visual observation of the product over time. Failure of the product to flush or properly clear the plumbing suggest problems in an actual use situation.

Sample flushing is done using a Kohler 1.6-gallon low water flow fixture and a 4" in-home piping system with approximately 35 feet of clear pipe area for product flow observations. The in-home piping system is designed using clear plastic pipe in 8 feet sections joined by standard 4" PVC fittings. The system is setup to conform to minimum design standards from the Universal Plumbing Code and BOCA code for wastewater flow.

Water and product movement is supported by gravitational force on the waste products. The piping system also has a flow valve to allow water to be introduced into the piping to clear clogged or stranded materials from the flush test.

The protocol involves placing individual interlabial pads into a fixture bowl (pads only, no toilet paper or simulated BM) and evacuating the bowl with 1.6 gallons of water. The pad must completely clear the fixture with an internal water trap without clogging the flow of the water and waste as it moves to the delivery piping. There should be no residual accumulation of the product in any of the system components.

After flushing and collecting the pads, they are transferred to a container of water for observation at 4 hours, 24 hours, and 7 days.

Equipment
Fixture—Kohler low water flow 1.6 gallon
In-home Piping System—4" clear plastic pipe (polycarbonate)
Collection screen—Stainless steel ¼" mesh or multi level sieve screen
Plastic container with lid (Sterlite® 28 qt., 23-¼ in.×17 in.×6 in.) Note: The minimum dimensions of the container are important. There must be enough room for all of the pads to float without touching each other. The water depth needs to be a minimum of 1½ inches greater than the products' length.
Plastic white 8" stir stick
Sampling and Test Procedure
All pads from each code (sample) should be tested in the same day.

Ensure that the containers are clean by wiping them out with a clean, dry cloth after each 7 day test. Do not use detergent or soap to clean the containers as it may affect the test results.

1) Select a code for testing and number each pad on both sides (cover and baffle).
2) Fold pad in half lengthwise, cover side out. Place the folded pad between the index and middle finger. With arm resting on the toilet seat, open fingers to drop 1 pad into the bowl. Note if it lands cover up or cover down. Wait for 30 seconds, then flush. Note if the product does not clear the bowl on the first flush. If necessary, flush a second time to clear the product from the bowl.
3) Repeat step 2 until 10 pads are flushed.
4) Inspect the collection screen to ensure that all the pads were collected. If any of the pads were hung-up in the system, add more water to the system by flushing or opening a valve to drive out the pads that did not initially clear the system. Note the number and location of the pads that got hung up in the system.
5) Add water, from the collection tank, to the container to fill it ½ inch from the top (=5½ inch water level). Ensure that containers have been wiped clean before starting.
6) Visually inspect each pad and transfer it to the container to which water had previously been added. Note which pads if any, had open seals, location of the open seals or if the product is coming apart in any way. When transferring pad to container, position the pad horizontally (cover side up on even # pads and baffle side up on odd # pads), grasp the pad in the center with thumb and finger, submerge the pad halfway below the surface of water then let go of pad. Place all pads from the same code in one container. [Exception for large size: only place 15 pads in one container]. Label the container with the product code and time when pads were added. Put lid on the container.
7) Repeat steps 1-6 until all pads from the same code have been flushed.
8) 3½ hours to 4½ hours (if the time exceeds 4½ hours make a notation on the data sheet) after placing the last set of 10 pads of the same code in the container gently stir the pads 5 times with a plastic stir stick, wait 5 minutes. Note the extent to which the pads have separated into individual components or the extent of seal separation between the cover sheet and back sheet.
9) 23½ hours to 24½ hours (if the time exceeds 24½ hours make a notation on the data sheet) after placing the pads in the container, gently stir the pads 5 times with a plastic stir stick, wait 5 minutes, and note the number of pads still floating and any other visual assessments, including the extent to which the pads have separated into individual components.
10) 7 days after placing the pads in the container, gently stir the pads 5 times with a plastic stir stick and wait 5 minutes. Note the extent to which the pads have separated into individual components or the extent of seal separation between the cover sheet and back sheet. Note the location of the open seals and if the pads appear to have air trapped inside of them.
11) Pads may be saved for later inspection.

EXAMPLE 1

Interlabial absorbent articles were tested in accordance with the procedure set forth above. The articles measured 79 mm long by 69 mm wide. The articles consisted of a nonwoven cover, an absorbent layer of 70% cotton and 30% rayon, and a poly outer cover or "baffle." The first code articles (sample size 30 articles) were constructed with 7.5 gsm of National Starch 427A water soluble adhesive. The adhesive was sprayed onto the baffle (outer cover). The second code articles (sample size 30 articles) were constructed with 10.5 gsm of National Starch 427A water soluble adhesive sprayed onto the baffle. The codes were separately flushed and observed as set forth above.

First Code: All pads were completely separated into individual components (cover, absorbent layer, baffle) immediately after flushing. After 7 days, all baffles were still floating in container and 60%-70% of the absorbent layers had sunk.

Second Code: All pads were intact after flushing. After 4 hours, 19 pads had open seals but with all three components still intact, 10 pads had at least two components still attached, and 1 pad was completely intact.

EXAMPLE 2

Interlabial absorbent articles were tested in accordance with the procedure set forth above. The articles measured 75 mm long by 65 mm wide. The articles were generally oval with laterally extending wings. The articles consisted of a nonwoven PET/Rayon cover, an absorbent layer of 60% cotton and 40% Rayon, and a poly (PE) outer cover or "baffle." The first code articles (sample size 30 articles) were constructed with 8.0 gsm hot melt add-on of National Starch 34-731A time delay water soluble adhesive. The adhesive was sprayed onto the baffle (outer cover). The second code articles (sample size 30 articles) were constructed with 10.5 gsm of the National Starch 34-731A adhesive sprayed onto the baffle. The codes were separately flushed and observed as set forth above.

First Code: At 4 hours, 10 products had greater than 50% open seals; 20 remaining products had open seals between 2-49%. The results were the same at 24 hours. At 7 days, 22 products had greater than 50% open seals; 1 product was separated into two pieces; and 7 products had open seals between 2-49%.

Second Code: At 4 hours, 2 products had greater than 50% open seals; 27 products had open seals between 2-49%; and 1 product had no open seals. At 24 hours, 3 products had greater than 50% open seals; 26 products had open seals between 2-49%; and 1 product had no open seals.

It should be appreciated by those skilled in the art that various modifications and variations may be made to the embodiments of the invention illustrated or described herein without departing from the scope and spirit of the invention as set forth in the appended claims and their equivalents.

What is claimed is:

1. An interlabial absorbent article configured for disposition primarily within the vestibule of a female wearer, comprising:
a generally liquid permeable cover sheet;
a generally liquid impermeable back sheet;
an absorbent material disposed between said cover sheet and said back sheet; and
a time-delayed water soluble adhesive combination placed to join said cover sheet and said back sheet together with said absorbent material sandwiched therebetween, said adhesive combination configured so as to maintain structural integrity of said article for a time period of greater than two hours after said article is immersed in water by being flushed while ensuring that said article loses structural integrity within about 24-72 hours after immersion; and wherein said adhesive combination comprises an adhesive having a time release agent additive, said additive preventing said adhesive from substantially dissolving before said time period of greater than two hours.

2. The interlabial absorbent article as in claim 1, wherein said article breaks up such that said cover sheet separates completely from said back sheet.

3. The interlabial absorbent article as in claim 1, wherein said cover sheet is adhered to said back sheet with said adhesive combination around a circumference of said article, and said article breaks up such that said cover sheet separates from said back sheet around at least a portion of said circumference.

4. The interlabial absorbent article as in claim 3, wherein said absorbent material is dispersible in water and disperses out of said article upon said cover sheet and said back sheet separating.

5. The interlabial absorbent article as in claim 1, wherein said adhesive combination is applied between said absorbent material and said back sheet.

6. The interlabial absorbent article as in claim 1, wherein said adhesive combination is applied between said absorbent material and said cover sheet.

7. The interlabial absorbent article as in claim 1, wherein said adhesive combination is applied between said absorbent material and said cover sheet and said absorbent material and said back sheet.

8. The interlabial absorbent article as in claim 1, wherein said cover sheet is adhered to said back sheet with said adhesive combination around a circumference of said article.

9. The interlabial absorbent article as in claim 5, said adhesive combination is applied as a meltblown spray generally uniformly over an inner face of said back sheet.

10. The interlabial absorbent article as in claim 1, wherein said cover sheet is adhered to said back sheet with said adhesive combination around a circumference of said article, and said absorbent material is adhered to said back sheet with a water insoluble adhesive, said absorbent material being dispersible in water.

11. An interlabial absorbent article configured for disposition primarily within the vestibule of a female wearer, comprising:
a generally liquid permeable cover sheet;
a generally liquid impermeable back sheet;
an absorbent material disposed between said cover sheet and said back sheet;
a time-delayed water soluble adhesive combination placed to join said cover sheet and said back sheet together with said absorbent material sandwiched therebetween, said adhesive combination configured so as to maintain structural integrity of said article for a time period of greater than two hours after said article is immersed in water by being flushed while ensuring that said article loses structural integrity within about 24-72 hours after immersion;
wherein said adhesive combination comprises discrete areas of a water soluble adhesive interspaced between discrete areas of a water insoluble adhesive, said absorbent material being dispersible in water, and wherein a spacing exists between said discrete areas of water insoluble adhesive such that said absorbent material disperses through said spacings upon said water soluble adhesive dissolving; and
wherein said water soluble adhesive and said water insoluble adhesive are applied in an alternate stripe pattern.

12. The interlabial absorbent article as in claim 1, further comprising a water insoluble adhesive between two components of said article.

13. The interlabial absorbent article as in claim 12, wherein a water insoluble adhesive is disposed between said absorbent material and one of said back sheet and said cover sheet, and said water soluble adhesive combination is disposed between said absorbent material and the other of said cover sheet and said back sheet.

14. The interlabial absorbent article as in claim 1, wherein at least a portion of said article components are biodegradable.

15. The interlabial absorbent article as in claim 1, further comprising a soluble material layer disposed between said absorbent material and said back sheet, said water soluble adhesive disposed between said soluble material layer and said back sheet.

* * * * *